US012778761B2

(12) United States Patent
Wang et al.

(10) Patent No.: US 12,778,761 B2
(45) Date of Patent: Nov. 3, 2026

(54) PROSTHESIS SYSTEM FOR MINIMALLY INVASIVE FEMORAL HEAD REPLACEMENT SURGERY

(71) Applicants: Yingze Zhang, hijiazhuang (CN); Hebei Innovation Institute of Orthopedic Biomaterials and Technology, Shijiazhuang (CN)

(72) Inventors: Juan Wang, Shijiazhuang (CN); Yingze Zhang, Shijiazhuang (CN); Yonglong Li, Shijiazhuang (CN)

(73) Assignees: Yingze Zhang, Shijiazhuang City (CN); Hebei Innovation Institute of Orthopedic Biomaterials and Technology, Shijiazhuang City (CN)

( * ) Notice: Subject to any disclaimer, the term of this patent is extended or adjusted under 35 U.S.C. 154(b) by 526 days.

(21) Appl. No.: 18/466,148

(22) Filed: Sep. 13, 2023

(65) Prior Publication Data

US 2024/0091015 A1 Mar. 21, 2024

(30) Foreign Application Priority Data

Sep. 16, 2022 (CN) ......................... 202211131860.X

(51) Int. Cl.
*A61F 2/36* (2006.01)
*A61F 2/30* (2006.01)

(52) U.S. Cl.
CPC ........ *A61F 2/3603* (2013.01); *A61F 2/30749* (2013.01); *A61F 2002/30492* (2013.01);
(Continued)

(58) Field of Classification Search
CPC ................ A61F 2/3603; A61F 2/30749; A61F 2002/30492; A61F 2002/30507;
(Continued)

(56) References Cited

U.S. PATENT DOCUMENTS 5,112,333 A * 5/1992 Fixel .................... A61B 17/744
606/62
6,284,002 B1 * 9/2001 Sotereanos ........ A61B 17/1753
623/23.27

(Continued)

FOREIGN PATENT DOCUMENTS

CN 202619829 U 12/2012
CN 104168857 A 11/2014

(Continued)

OTHER PUBLICATIONS

1st Office Action dated Jan. 21, 2026 of Chinese Application No. 202211131860.X.

*Primary Examiner* — Eduardo C Robert
(74) *Attorney, Agent, or Firm* — Qinghong Xu

(57) ABSTRACT

A prosthesis system for minimally invasive femoral head replacement surgery includes a prosthesis having a first and second ends, a femoral head prosthesis being provided at the first end of the prosthesis, the prosthesis being provided with a nail hole, and the femoral head prosthesis partially protruding from the first end of the channel; an extension rod detachably and fixedly connected with the second end of the prosthesis; a guiding frame having a positioning sleeve and a guiding sleeve, the positioning sleeve being sleeved outside the extension rod and positioning the extension rod, after the extension rod is positioned, a center line of the guiding sleeve and a center line of the nail hole are on the same straight line; and a locking nail fixed to the nail hole of the prosthesis, both ends of the locking nail protruding out of the prosthesis.

12 Claims, 8 Drawing Sheets

(52) U.S. Cl.
CPC ............... *A61F 2002/30507* (2013.01); *A61F 2002/3055* (2013.01)

(58) Field of Classification Search
CPC . A61F 2002/3055; A61B 17/58; A61B 17/56; A61B 17/72; A61B 17/7233; A61B 17/7241; A61B 17/725; A61B 17/7283
USPC ............................................................ 606/89
See application file for complete search history.

(56) References Cited

U.S. PATENT DOCUMENTS

| | | | | |
|---|---|---|---|---|
| 8,491,584 | B1 * | 7/2013 | Fagan | A61B 17/7266 606/64 |
| 10,758,356 | B1 | 9/2020 | Sartawi | |
| 2007/0038306 | A1 | 2/2007 | O'Gara | |
| 2020/0323575 | A1 * | 10/2020 | Cortes Cubero | A61F 2/4637 |

FOREIGN PATENT DOCUMENTS

| | | | | | |
|---|---|---|---|---|---|
| CN | 207024106 | U | | 2/2018 | |
| CN | 108433799 | A | | 8/2018 | |
| CN | 110495939 | A | | 11/2019 | |
| CN | 113180815 | A | * | 7/2021 | A61B 90/11 |
| DE | 20007950 | U1 | * | 7/2000 | A61F 2/30721 |
| EP | 3777775 | A1 | * | 2/2021 | A61F 2/3603 |
| WO | 2019238992 | A1 | | 12/2019 | |

* cited by examiner

PROSTHESIS SYSTEM FOR MINIMALLY INVASIVE FEMORAL HEAD REPLACEMENT SURGERY

CROSS-REFERENCE TO RELATED APPLICATIONS

This application is based on and claims priority to the Chinese application No. 202211131860.X, filed on Sep. 16, 2022, the entire contents of which are incorporated herein by reference.

TECHNICAL FIELD

This disclosure relates to the technical field of a femoral head replacement, in particular to a prosthesis system for a minimally invasive femoral head replacement surgery.

BACKGROUND

Osteonecrosis of a femoral head refers to a disease in which blood supply of the femoral head is interrupted or damaged, resulting in death of bone cells and bone marrow components, and then leading to structural changes of the femoral head, collapse of the femoral head and joint dysfunction. An artificial femoral head replacement is generally used by implanting an artificial prosthesis for a patient to replace the diseased femoral head, to restore normal anatomical relationship of a hip joint, improve joint mobility and relieve pain.

In a conventional replacement surgery of an artificial femoral head including or excluding a femoral stem prosthesis, an excision site, as shown in FIG. 1, refers to a neck part and the femoral head 012 that have been affected or worn, which is obtained by directly cutting off the femoral head 013 obliquely along a base of a femoral head neck part 011, as shown by a cutting line L1, hollowing out and expanding a femoral medullary cavity before implanting and fixing an artificial femoral stem prosthesis to be combined with an artificial femoral head 02. According to US patent (U.S. Pat. No. 5,163,961A) and CN Patent (CN00244070.9), it is disclosed that the affected or worn femoral head 012 is removed from the femoral neck, and a cover 03 is secured to the residual femoral neck 011 by bolts.

However, in practical use, the above-mentioned surgical method has following disadvantages.

1) As it is necessary to remove a large area of bones, remove the bone marrow components, and reshape during the replacement surgery of the artificial hip joint including the femoral stem prosthesis, the severity of injury, duration of the operation, and blood loss can be significantly increased. Moreover, severing the posterior lateral muscle group can increase the risk of dislocation, thereby further increasing an overall surgical risk.
2) Since the removal of a large area of bones (i.e., all of the femoral neck) is a factor that makes the related dimensional accuracy difficult to control, maintaining a matching accuracy between the surface of the artificial hip joint including the femoral stem prosthesis or the inner surface of the cover body of the artificial hip joint excluding the femoral stem prosthesis and the surface of the bone to be installed is difficult. The artificial hip joint may not achieve stable bonding support by means of harder bone or the surface of the neck part, and as a result, it is prone to stress concentration. This can directly and seriously affect the surgical results and the quality of surgical recovery.
3) Due to limited service life of various artificial joints, a revision surgery must be operated under the circumstances that complications such as worn, loosening, and sinking usually occur after a long-term use. However, the conventional replacement surgery of the artificial hip joint including the femoral stem prosthesis requires further enlargement and deepening of the entire femoral medullary cavity in the process of the revision surgery due to the initial surgical resection and the severity of injury in a large area, in this way, it is inevitable to increase the injury and difficulty of the operation. Moreover, since a wear cycle of the prosthesis is approximately 30 years, it poses challenges for younger patients and there are limited options for revision surgery once the prosthesis does not work.
4) Due to the lack of a scientific, comprehensive, and clear measuring and positioning method and procedure for the bone resection site in the conventional replacement surgery of an artificial hip joint excluding the femoral stem prosthesis, the determination of the resection site in the femoral neck relies on the operator's experiences. As a result, the postoperative results can vary significantly among different operators, making it difficult to ensure the consistency in the procedure. Consequently, it becomes difficult to simulate and evaluate the success or failure of the operation in advance, and psychological preparation for patients before the operation becomes challenging.
5) As shown in FIG. 1, the oblique arrangement of the cover 03 in the artificial hip joint excluding the femoral stem prosthesis on the cutting plane of the parallel cutting line L1 can lead to a discontinuous and imperfect fit between the surface of the femoral neck 011 and the inner surface of the cover 03. Consequently, joint stress may not be evenly distributed and conducted, resulting in stress concentration during practical use. This can negatively impact the overall durability of the structure.

In view of the above disadvantages of the conventional replacement surgery for the hip joint, it is necessary to develop a prosthesis system to overcome the disadvantages.

SUMMARY

A technical problem to be solved by the present disclosure is to provide a prosthesis system for minimally invasive femoral head replacement surgery, which can reduce the injury of the femoral head replacement and improve the stability of prosthesis implantation.

In order to solve the technical problem, the technical solution as adopted by the present disclosure is as follows:

According to one aspect of the present disclosure, a prosthesis system for minimally invasive femoral head replacement surgery includes:

a prosthesis, configured to fill in a channel in a direction of a femoral neck, the prosthesis having a first end and a second end opposite to each other, a femoral head prosthesis being provided at the first end of the prosthesis, the prosthesis being provided with a nail hole penetrating radially, and the femoral head prosthesis partially protruding from the first end of the channel;

an extension rod, detachably and fixedly connected with the second end of the prosthesis;

a guiding frame, a positioning sleeve and a guiding sleeve being arranged on the guiding frame, the positioning sleeve being sleeved outside the extension rod and positioning the extension rod, after the extension rod is positioned, a center line of the guiding sleeve and a center line of the nail hole are on the same straight line; and a locking nail, fixed to the nail hole of the prosthesis, and both ends of the locking nail protruding out of the prosthesis.

According to an embodiment of the present disclosure, the guiding frame has a U-shaped structure having a connecting end and a free end opposite to each other, the positioning sleeve is arranged at the connecting end, and the guiding sleeve is arranged at the free end.

According to an embodiment of the present disclosure, the locking nail has a hollow structure.

According to an embodiment of the present disclosure, external threads are provided on an outer surface of the locking nail.

According to an embodiment of the present disclosure, an inner hole at a rear end of the locking nail is in a non-circular structure, and the prosthesis system further comprises:

a rotary cylinder, sleeved in the guiding sleeve, and having a front end at which a rotary head embedded in the inner hole of the locking nail is provided; and a guide pin, inserted into the rotary cylinder and the locking nail.

According to an embodiment of the present disclosure, a dial scale and a pointer capable of rotating and locking are further provided on the guiding frame.

According to an embodiment of the present disclosure, the prosthesis has a hollow structure.

According to an embodiment of the present disclosure, the prosthesis is a cage with holes on the outer wall, or no hole is provided at the outer wall of the prosthesis.

According to an embodiment of the present disclosure, the femoral head prosthesis comprises a ball head integrally formed with the prosthesis and an outer cup arranged outside the ball head.

According to an embodiment of the present disclosure, a silica gel column is arranged between the ball head and the outer cup, and the silica gel column protrudes out of an outer surface of the ball head.

According to the other aspect of the present disclosure, a prosthesis system for minimally invasive femoral head replacement surgery serves as a channel in a direction of the femoral neck, and the channel has a first end penetrating the superficial layer of the femoral head, and a second end penetrating in an opposite direction; including:

a prosthesis, filled in a channel, a femoral head prosthesis being provided at the first end of the prosthesis, the prosthesis being provided with a nail hole penetrating radially, and the femoral head prosthesis partially protruding from the first end of the channel;

an extension rod, detachably and fixedly connected with the second end of the prosthesis;

a guiding frame, a positioning sleeve for positioning the extension rod, a guiding sleeve for guiding the locking nail, after the positioning sleeve is in cooperation with the extension rod, the extension rod is rotated and positioned at an axial position, and after the extension rod is positioned, the guiding sleeve is directed to the nail hole; and a locking nail, passing through the nail hole on the prosthesis via the guiding sleeve to be fixed to the prosthesis, and both ends of the locking nail being connected with and fixed to cortical layers of a greater trochanter and a lesser trochanter of a femur.

According to an embodiment of the present disclosure, the prosthesis has a hollow structure, having external threads.

According to an embodiment of the present disclosure, the prosthesis system for minimally invasive femoral head replacement surgery further includes:

a guide pin, driven through the guiding sleeve, passing through the nail hole from the greater trochanter of femur and penetrating the cortical layer of the lesser trochanter of femur;

a locking nail, sleeved outside the guide pin and driven along the guide pin, wherein the inner hole at the rear end of the locking nail is in a non-circular structure; and a rotary cylinder, sleeved outside the guide pin, wherein the front end of the rotary cylinder is provided with a rotary head embedded with the inner hole of the lock nail, and the lock nail is driven by the rotary cylinder to be driven.

According to an embodiment of the present disclosure, the guiding sleeve, the locking nail and the nail hole are configured in two sets.

According to an embodiment of the present disclosure, the two sets of the guiding sleeves, the locking nails and the nail holes are parallel to each other and positioned within the same plane; or the two sets of the guiding sleeves, the locking nails and the nail holes are not parallel.

According to an embodiment of the present disclosure, a distance between the two sets of the nail holes is 5-30 mm, and a diameter of the nail hole is 3-8 mm.

According to an embodiment of the present disclosure, a notch is provided at a rear end of the positioning sleeve, and a protrusion is provided at an outer wall of the extension rod, and the protrusion is embedded in the notch and radially protruded out of the notch.

According to an embodiment of the present disclosure, a pointer capable of rotating and locking is further provided on the guiding frame.

According to an embodiment of the present disclosure, the prosthesis is hollow, a cage-like structure with an outer wall having holes, or a hollow, a structure with a solid outer wall.

According to an embodiment of the present disclosure, a plurality of barb structures for preventing outward axial movement of the prosthesis are provided on an outer wall of the prosthesis.

According to an embodiment of the present disclosure, the femoral head prosthesis includes a ball head integrally formed with the prosthesis and an outer cup arranged outside the ball head, and a silica gel column is provided between the ball head and the outer cup.

The beneficial effects generated by the technical solution are:

The femoral head replacement surgery performed using the prosthesis system described in the present disclosure involves making a small incision on an outer side of the femoral neck. A channel is then created, and a prosthesis is implanted into the channel. This eliminates the need for removing the femoral head and the femoral neck, as well as hollowing out the femoral medullary cavity. As a result, the severity of the injury, the duration of the operation, and the amount of blood loss can be significantly reduced.

A detachable extension rod is arranged on the implanted prosthesis, and after the extension rod and the guiding frame are matched and positioned, the driving path of the locking nail can be guided, so that after the locking nail is connected with the prosthesis, it can be fixed with the greater trochanter and the lesser trochanter of the patient, so that the prosthesis can be combined with the hard bone and the surface layer of the femoral neck, so as to achieve stable combined support and avoid loosening of the prosthesis.

The minimally invasive femoral head replacement surgery implemented using the prosthesis system can be effectively revised when the prosthesis is worn out. Therefore, it is more beneficial for patients with the femoral head conditions.

BRIEF DESCRIPTION OF THE DRAWINGS

The present disclosure will be further described in detail with reference to the attached drawings and specific embodiments.

DETAILED DESCRIPTION

Hereinafter, the technical solutions in the embodiments of the present disclosure will be clearly and completely described in combination with the accompanying drawings. Obviously, the embodiments as described are merely a part of the embodiments, but not all of the embodiments of the present disclosure. Other embodiments obtained by the person skilled in the art without any creative effort are within the scope of the present disclosure.

In order to understand the disclosure fully, many specific details are set forth in the following description, besides other implementation that are different from those described herein may be adopted, that is, those skilled in the art could make similar modification without violation of the present disclosure. The present disclosure therefore is not limited to the specific embodiments below.

Figure 1:
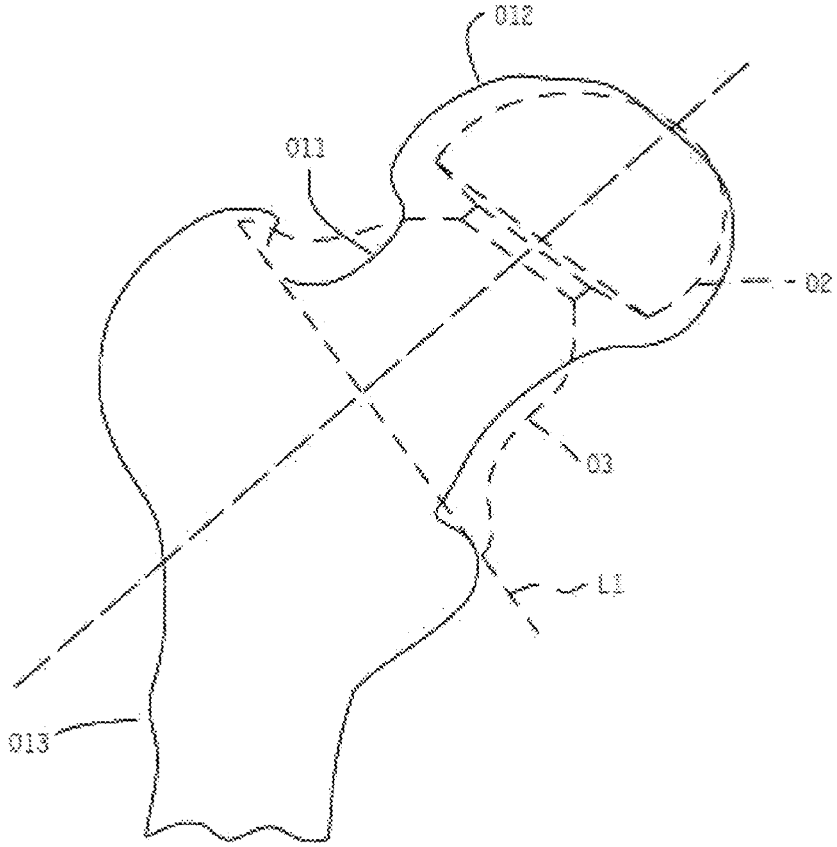
FIG.1 (Prior Art)
FIG. 1 shows a cutting position of a femoral head in which a replacement surgery is implemented in the related art.
Figure 2:
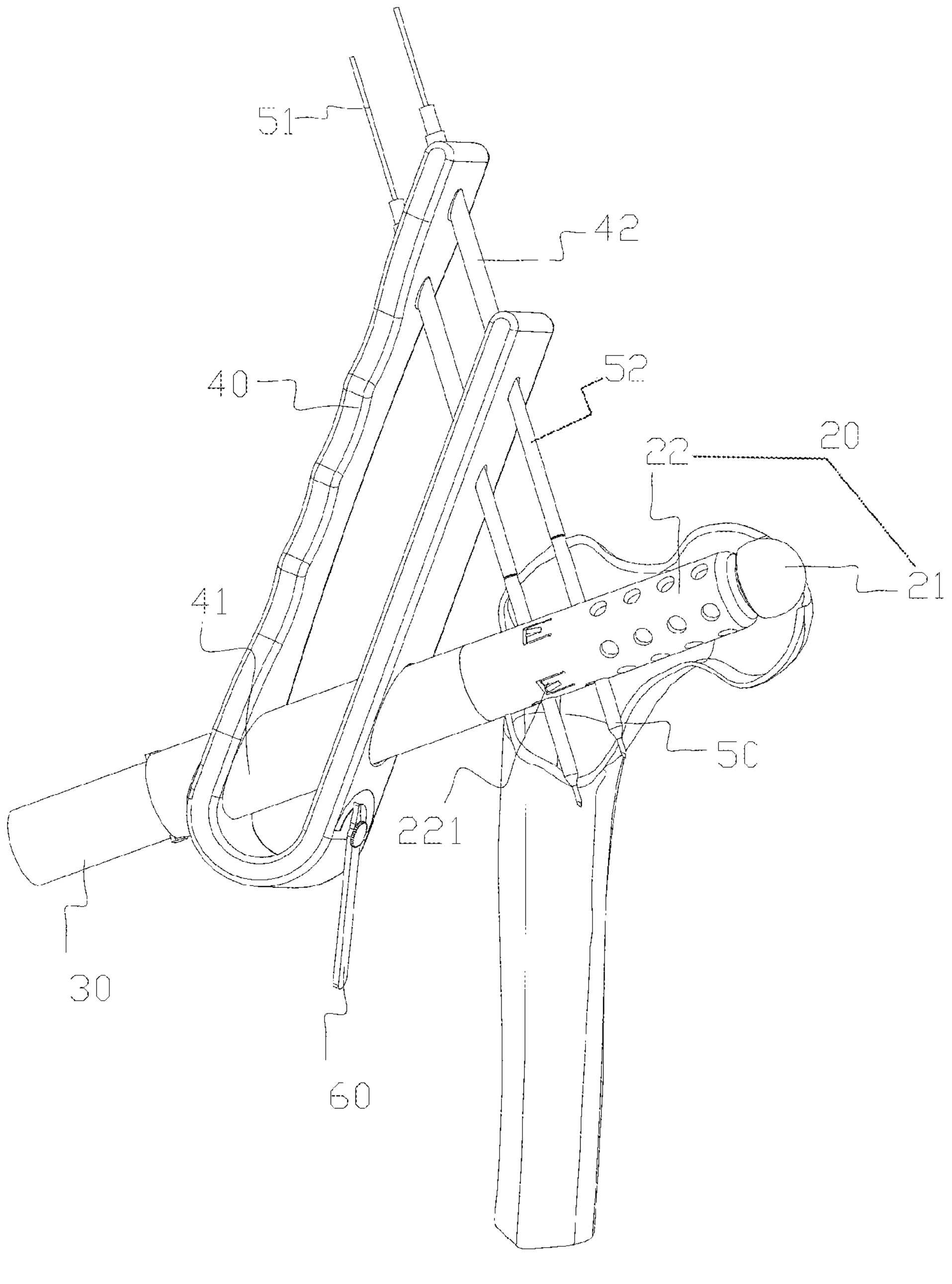
FIG. 2 shows a schematic view of a use state of a prosthesis system of the present disclosure during surgery.
Figure 3:
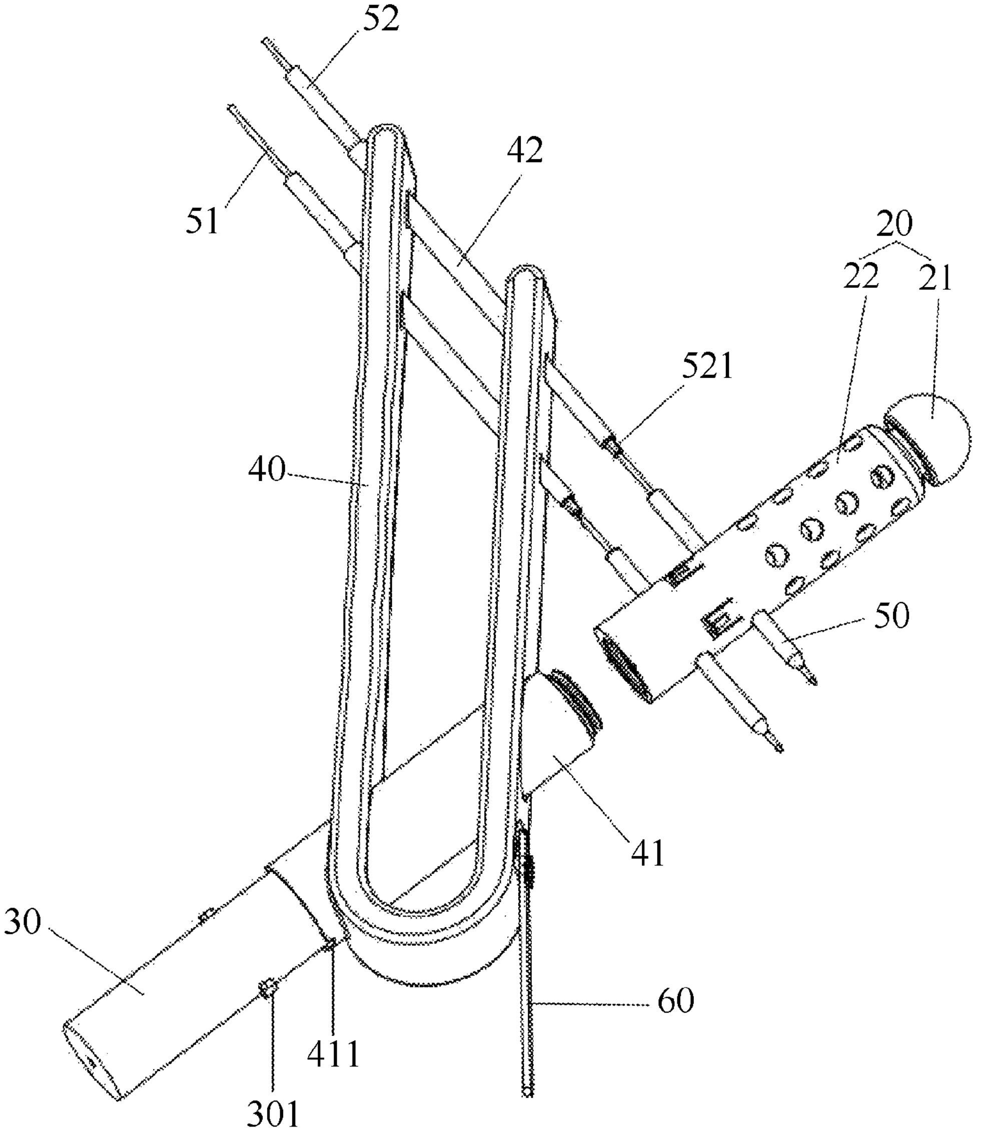
FIG. 3 shows a schematic view of an explosion structure of the prosthesis system of the present disclosure.
Figure 4:
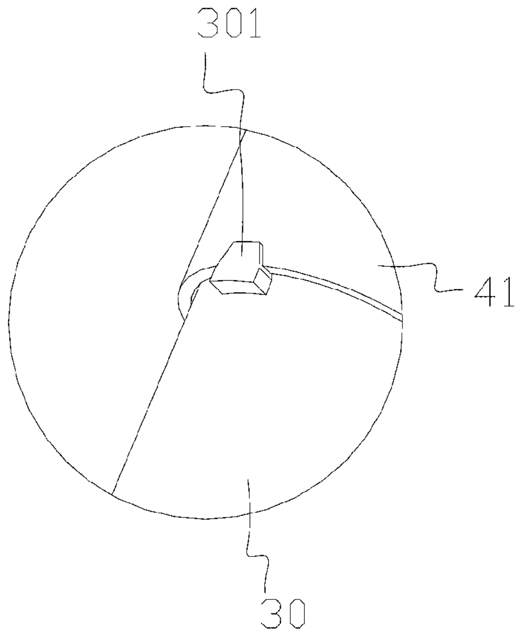
FIG. 4 shows the structural schematic view of a positioning sleeve and a locking part of the extension rod in the prosthesis system of the present disclosure.
Figure 5:
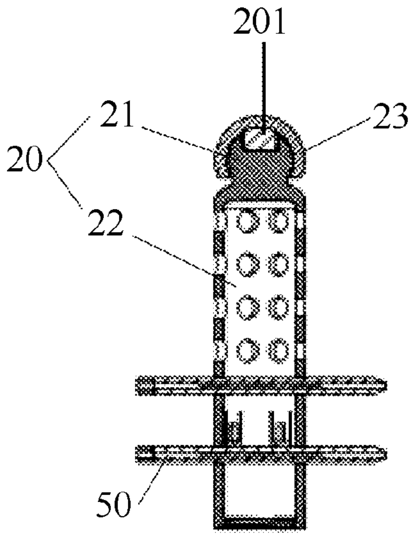
FIG. 5 shows a structure I of a prosthesis in the prosthesis system of the present disclosure.
Figure 6:
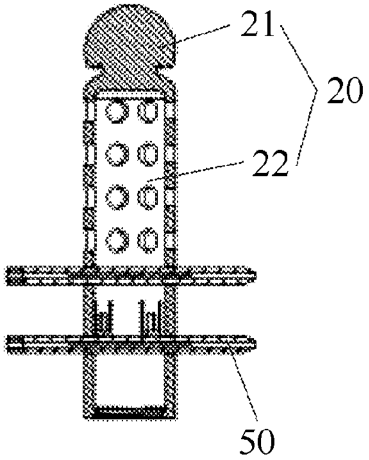
FIG. 6 shows a structure II of the prosthesis in the prosthesis system of the present disclosure.
Figure 7:
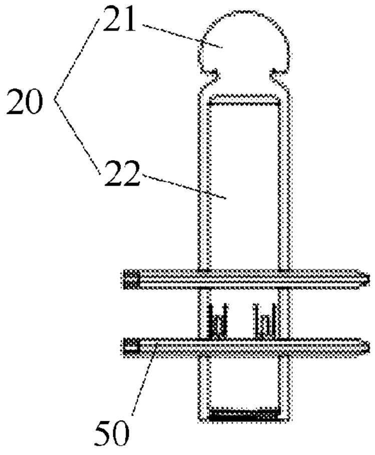
FIG. 7 shows a structure III of the prosthesis in the prosthesis system of the present disclosure.
Figure 8:
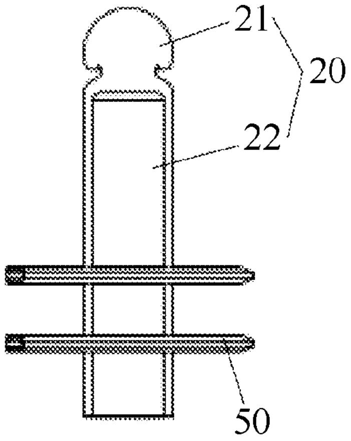
FIG. 8 shows a structure IV of the prosthesis in the prosthesis system of the present disclosure.

As shown in FIGS. 2-4, a prosthesis system for minimally invasive femoral head replacement surgery of the present disclosure includes a prosthesis 20, an extension rod 30, a guiding frame 40 and a locking nail 50.

In the minimally invasive femoral head replacement surgery by using the prosthesis system of the present disclosure, a channel in a direction of the femoral neck may be established by using a bone cutting assembly. The bone cutting assembly creating the channel in orthopedics is of the prior art, in various forms, and the channel may be created by using tools such as a bone drill, a circular cutter and a scraper. The first end of the channel passes through a superficial layer of the femoral head, and the second end thereof passes through in an opposite direction.

The prosthesis 20 is filled in the channel. The femoral head prosthesis 21 is provided at a first end of the prosthesis 20. A nail hole is disposed in and longitudinally passes through the prosthesis. The femoral head prosthesis 21 partially protrudes from the first end of the channel to contact with an acetabulum. The extension rod 30 is detachably fixed to the second end of the prosthesis 20, and specific connection may be threaded connection or other quick detachable structures.

The guiding frame 40 includes a positioning sleeve 41 for positioning the extension rod 30 and a guiding sleeve 42 for guiding the locking nail 50. Specifically, a notch 411 is provided at a rear end of the positioning sleeve 41, and a protrusion 301 is provided on an outer wall of the extension rod 30, and the protrusion 301 may be embedded in the notch 411 and protrude radially from the notch 411, so that the positioning sleeve 41 can be in cooperation with the extension rod 30, that is, the positioning sleeve 41 can rotate and position the extension rod 30 in an axial position. After the extension rod 30 (i.e., the prosthesis 20) is positioned, the guiding sleeve 42 can be directed to the nail hole.

The locking nail 50 passes through the nail hole of the prosthesis 20 through the guiding sleeve 42 and then secures to the prosthesis 20, and both ends of the locking nail 50 can be connected and fixed with cortical layers of the greater trochanter and the lesser trochanter of the femur. The locking nail 50 may have a hollow structure with external threads, and the nail hole on the prosthesis may be a smooth hole or a threaded hole. The external threads on the locking nail 50 are configured to mainly increase a friction force between the bone and the locking nail 50 and thereby increasing a holding force of the bone against the locking nail 50.

A prosthesis system for minimally invasive femoral head replacement surgery according to an embodiment of the present disclosure further includes components, such as a guide pin 51 and a rotary cylinder 52 for installing the locking nail 50. The guide pin 51 is driven via the guiding sleeve 42 through the nail hole via the greater trochanter of the femur and through the cortical layer of the lesser trochanter of the femur. The locking nail 50 is sleeved outside the guide pin 51 and driven along the guide pin 51, and an inner hole at the rear end of the locking nail 50 has a non-circular structure. The rotary cylinder 52 is sleeved outside the guide pin 51, and the front end of the rotary cylinder 52 has a rotary head 521 fitted into the inner hole of the locking nail 50, and the locking nail 50 is driven by the rotation and driving of the rotary cylinder 52. Such structure is configured such that a length of the locking nail 50 may not be designed too long as long as it can meet the requirement for the surgery, and the excess length of the locking nail 50 may be cut off in follow-up procedure in which no tools are required, so that the operation efficiency can be improved.

In the prosthesis system for minimally invasive femoral head replacement surgery, two sets of guiding sleeves 42, locking nails 50 and nail holes are provided, and the two sets are parallel to each other and located in the same plane, so that the connection strength between the locking nails 50 and the bones can be enhanced. In addition, a distance between the two sets of nail holes is 5~30 mm, and a diameter of the nail hole is 3~8 mm, so that a firm connection between the prosthesis 20 and the bones can be ensured. In other embodiments, the two sets of guiding sleeves 42, locking nails 50 and nail holes are not in parallel.

An operation method of the prosthesis system for minimally invasive femoral head replacement surgery is described as follows:

1. Creating a channel, a patient's leg portion is pulled in an affected area, a gap of an acetabular is opened, and a dead bone dense area is positioned according to a preoperative planning data, a tip of a guide pin is guided toward the dead bone dense area, and the guide pin for positioning is driven from the greater trochanter to an inferior cortex along a direction of the femoral neck, after the position of the guide pin is determined, a channel in the direction of the femoral neck is created by used of a bone cutting component (such as a guide trephine), so that the second end of the channel penetrates through the surface layer of the greater trochanter of the femur and the first end thereof penetrates a cartilage layer of the femoral head.

2. Assembling, the prosthesis 20 is connected with the extension rod 30, and the extension rod 30 is connected with the positioning sleeve 41 on the guiding frame 40, so that the guiding sleeve 42 on the guiding frame 40 is directed to the nail hole of the prosthesis 20.
3. Implanting the prosthesis 20, the prosthesis 20 is implanted into the channel, deepened into a proper position in a perspective environment, so that the femoral head prosthesis 21 partially protrudes from the first end of the channel to contact with the acetabulum.
4. Adjusting the position, it including the prosthesis 20, the extension rod 30 and the guiding frame 40 is rotated entirely, so that the guiding sleeve 42 at the outer side is directed to the greater trochanter of the patient's femur.
5. Driving the locking nail 50, the guide pin 51, for example, Kirschner wire, is driven from the greater trochanter of femur along the guiding sleeve 42, to allow the front end of the guide pin 51 to pass through the lesser trochanter of the femur in the perspective environment, and then the locking nail 50 is inserted along the guide pin 51, the rotary cylinder 52 is put onto the guide pin 51, and a rotary head 521 of the rotary cylinder 52 is inserted into an inner hole at the rear end of the locking nail 50, the locking nail 50 may be rotated by rotating the rotary cylinder 52 to pass through the nail hole of the prosthesis so as to secured to the prosthesis, and in the perspective environment, the front end of the locking nail 50 is connected with and fixed to the cortical layer of the lesser trochanter of the femur.
6. Removing redundant parts, the guide pin 51, the rotary cylinder 52, the extension rod 30 and the guiding frame 40 are removed.
7. Stitching, the operation is completed.

In the case that the femoral head replacement surgery is operated by using the prosthesis system according to the present disclosure, only a small opening is created on the outer side of the femoral neck, and then a channel is created, and finally the prosthesis 20 is implanted in the channel, so that it is not necessary to cut off the femoral head and the femoral neck, or to hollow out the femoral marrow cavity. This can bring about advantage that the severity of injury is low, the duration of the operation is short, and the blood loss is greatly reduced.

A detachable extension rod 30 is arranged on the implanted prosthesis 20. The extension rod 30 is matched and positioned with the guiding frame 40 to guide a path along which the locking nail 50 is driven, so that the locking nail 50 is connected with the prosthesis 20 to be fixed with the patient's greater trochanter and lesser trochanter, and the prosthesis 20 can be combined with the hard bone and the surface layer of the femoral neck to achieve stable combination and support and avoid the loosening of the prosthesis 20.

The minimally invasive femoral head replacement surgery performed using this component allows for the effective revision of the prosthesis 20 that has been worn. It is more patient-friendly for patients having the femoral head conditions.

In the prosthesis system for minimally invasive femoral head replacement surgery of the present disclosure, a pointer 60 that is capable of rotating and locking is further provided on the guiding frame 40, and the pointer 60 is provided with a dial scale. Before the operation, a doctor pre-adjusts an angle between the pointer 60 and the guiding frame 40 according to an angle formed by the trochanter and the femoral diaphysis. The femoral diaphysis is regarded as a reference, when the pointer 60 is parallel to the femoral diaphysis, the guiding sleeve 42 on the guiding frame 40 points to the position of the trochanter at this time. In order to facilitate the operation of the above-mentioned the step 4 of the surgery, this function is combined with the precise medical preoperative planning technology advocated by the modern medicine, which can reduce the times of fluoroscopy.

In the prosthesis system for minimally invasive femoral head replacement surgery, as shown in FIGS. 5-8, the prosthesis 20 may be made of metal materials such as pure titanium, stainless steel, cobalt-based alloy, titanium-based alloy, magnesium-titanium alloy, or non-degradable polymer materials such as PA plastics and polyethylene (PE).

The wear between the femoral head prosthesis and the acetabulum can be reduced by implanting the femoral head prosthesis through a femoral neck channel. As shown in FIGS. 5 to 8, the prosthesis 20 may include a femoral head prosthesis 21 and a femoral neck prosthesis 22, which may be an integrated structure, wherein the femoral head prosthesis 21 may be bipolar or unipolar. The femoral neck prosthesis 22 may have a hollow structure, and the femoral neck prosthesis 22 may have a plurality of regular holes or irregular holes on the outer wall thereof.

For young and highly active patients, the prosthetic 20 may be selected preferably from a hollow and perforated cage structure. The cage can accommodate autologous bones or artificial bones, which can promote local bone growth and ensure femoral bone vitality to the largest extent and can also enhance the fixation between the bone and the implantation and thus is suitable for young patients who require secure fixation of the prosthetic 20. Furthermore, a plurality of barb structures 221 for preventing the outward axial movement of the prosthesis 20 may be provided on the outer wall of the prosthetic 20. The barb structures 221 are limited by the hard bone tissues on the inner wall of the channel, to strengthen the implantation stability of the prosthesis 20.

For older patients with osteoporosis, the prosthesis 20 is preferably selected to be in the form of a hollow structure without holes in the outer wall.

In addition, the femoral head prosthesis 21 may be a ball head. An outer cup 23 may be arranged outside the ball head, and a silica gel column 201 is arranged between the ball head and the outer cup, specifically, a sink is formed at the front end of the ball head, and the silica gel column 201 is filled and protruded from the sink and contacted with the outer cup 23. The silica gel column 201 has axial compression and performs cushioning effect. This is beneficial to reduce the wear of the femoral head prosthesis 21 and prolong the service life of the femoral head prosthesis 21, and it is more suitable for young and highly active patients.

The above is merely a preferred embodiment of the present invention. Any slight modifications, variations, or equivalent replacements made by anyone in accordance with the present disclosure are within the protection scope of the present disclosure.

What is claimed is:

1. A prosthesis system for minimally invasive femoral head replacement surgery, comprising:

a prosthesis, configured to fill in a channel in a direction of a femoral neck, the prosthesis having a first end and a second end opposite to each other, a femoral head prosthesis being provided at the first end of the prosthesis, the prosthesis being provided with a nail hole penetrating radially with respect to a longitudinal axis of the prosthesis, and the femoral head prosthesis is adapted to partially protrude from a first end of the channel;

an extension rod, detachably and fixedly connected with the second end of the prosthesis;

a guiding frame;

a positioning sleeve and a guiding sleeve being arranged on the guiding frame, the positioning sleeve being sleeved outside the extension rod such that a center line of the guiding sleeve and a center line of the nail hole are on a same straight line after the extension rod is positioned by the positioning sleeve; and a locking nail, configured to be fixed to the nail hole of the prosthesis, and both ends of the locking nail protruding out of the prosthesis, wherein the locking nail has a hollow structure; and an inner hole at a rear end of the locking nail is in a non-circular structure, and the prosthesis system further comprises:

a rotary cylinder, configured to sleeve in the guiding sleeve, a rotary head is provided at front end of the rotary cylinder, the rotary head is embedded in the inner hole of the locking nail; and a guide pin, configured to insert into the rotary cylinder and the locking nail.

2. The prosthesis system for minimally invasive femoral head replacement surgery according to claim 1, wherein the guiding frame has a U-shaped structure having a connecting end and a free end opposite to each other, the positioning sleeve is arranged at the connecting end, and the guiding sleeve is arranged at the free end.

3. The prosthesis system for minimally invasive femoral head replacement surgery according to claim 2, wherein external threads are provided on an outer surface of the locking nail.

4. The prosthesis system for minimally invasive femoral head replacement surgery according to claim 1, wherein the guiding sleeve, the locking nail and the nail hole are configured in two sets.

5. The prosthesis system for minimally invasive femoral head replacement surgery according to claim 4, wherein the two sets of the guiding sleeves, the locking nails and the nail holes are parallel to each other and positioned within the same plane; or the two sets of the guiding sleeves, the locking nails and the nail holes are not parallel.

6. The prosthesis system for minimally invasive femoral head replacement surgery according to claim 4, wherein a distance between the two sets of the nail holes is 5-30 mm, and a diameter of the nail hole is 3-8 mm.

7. The prosthesis system for minimally invasive femoral head replacement surgery according to claim 1, wherein the prosthesis has a hollow structure.

8. The prosthesis system for minimally invasive femoral head replacement surgery according to claim 7, wherein the prosthesis is a cage with holes on the outer wall, or no hole is provided at the outer wall of the prosthesis.

9. The prosthesis system for minimally invasive femoral head replacement surgery according to claim 1, wherein a plurality of barb structures for preventing outward axial movement of the prosthesis are provided on an external surface of the prosthesis.

10. A prosthesis system for minimally invasive femoral head replacement surgery, comprising:

a prosthesis, configured to fill in a channel in a direction of a femoral neck, the prosthesis having a first end and a second end opposite to each other, a femoral head prosthesis being provided at the first end of the prosthesis, the prosthesis being provided with a nail hole penetrating radially with respect to a longitudinal axis of the prosthesis, and the femoral head prosthesis is adapted to partially protrude from a first end of the channel;

an extension rod, detachably and fixedly connected with the second end of the prosthesis;

a guiding frame;

a positioning sleeve and a guiding sleeve being arranged on the guiding frame, the positioning sleeve being sleeved outside the extension rod, such that a center line of the guiding sleeve and a center line of the nail hole are on a same straight line after the extension rod is positioned by the positioning sleeve; and a locking nail, configured to be fixed to the nail hole of the prosthesis, and both ends of the locking nail protruding out of the prosthesis, wherein a notch is provided at a rear end of the positioning sleeve, and a protrusion is provided at an outer wall of the extension rod, and the protrusion is embedded in the notch and radially protruded out of the notch.

11. A prosthesis system for minimally invasive femoral head replacement surgery, comprising:

a prosthesis, configured to fill in a channel in a direction of a femoral neck, the prosthesis having a first end and a second end opposite to each other, a femoral head prosthesis being provided at the first end of the prosthesis, the prosthesis being provided with a nail hole penetrating radially with respect to a longitudinal axis of the prosthesis, and the femoral head prosthesis is adapted to partially protrude from a first end of the channel;

an extension rod, detachably and fixedly connected with the second end of the prosthesis;

a guiding frame;

a positioning sleeve and a guiding sleeve being arranged on the guiding frame, the positioning sleeve being sleeved outside the extension rod, such that a center line of the guiding sleeve and a center line of the nail hole are on a same straight line after the extension rod is positioned by the positioning sleeve; and a locking nail, configured to be fixed to the nail hole of the prosthesis, and both ends of the locking nail protruding out of the prosthesis, wherein a dial scale and a pointer capable of rotating and locking are further provided on the guiding frame.

12. A prosthesis system for minimally invasive femoral head replacement surgery, comprising:

a prosthesis, configured to fill in a channel in a direction of a femoral neck, the prosthesis having a first end and a second end opposite to each other, a femoral head prosthesis being provided at the first end of the prosthesis, the prosthesis being provided with a nail hole penetrating radially with respect to a longitudinal axis of the prosthesis, and the femoral head prosthesis is adapted to partially protrude from a first end of the channel;

an extension rod, detachably and fixedly connected with the second end of the prosthesis;

a guiding frame;

a positioning sleeve and a guiding sleeve being arranged on the guiding frame, the positioning sleeve being sleeved outside the extension rod, such that a center line of the guiding sleeve and a center line of the nail hole are on a same straight line after the extension rod is positioned by the positioning sleeve; and a locking nail, configured to be fixed to the nail hole of the prosthesis, and both ends of the locking nail protruding out of the prosthesis, wherein the femoral head prosthesis comprises a ball head integrally formed with the prosthesis and an outer cup arranged outside the ball head, and wherein a silica gel column is arranged between the ball head and the outer cup, and the silica gel column protrudes out of an outer surface of the ball head.

* * * * *